United States Patent [19]

Horwell et al.

[11] Patent Number: 5,051,428

[45] Date of Patent: Sep. 24, 1991

[54] 2-AMINO-4 OR 5-METHOXYCYCLOHEXYL AMIDES USEFUL AS ANALGESICS

[75] Inventors: David C. Horwell; David C. Rees, both of Cambridge, England

[73] Assignee: Warner-Lambert Company, Morris Plains, N.J.

[21] Appl. No.: 503,067

[22] Filed: Mar. 29, 1990

Related U.S. Application Data

[63] Continuation of Ser. No. 280,759, Dec. 6, 1988, abandoned.

[51] Int. Cl.⁵ ............... C07D 207/6; A61K 31/34; A61K 31/38; A61K 31/40
[52] U.S. Cl. ................... 514/320; 514/324; 514/422; 514/443; 514/467; 514/469; 548/525; 549/57; 549/58
[58] Field of Search ............ 548/525; 549/57, 58; 514/467, 320, 324, 422, 443, 469

[56] References Cited

U.S. PATENT DOCUMENTS

| | | | |
|---|---|---|---|
| 4,098,904 | 7/1978 | Szmuszkovicz | 424/324 |
| 4,145,435 | 3/1979 | Szmuszkovicz . | |
| 4,212,878 | 7/1980 | Lednicer . | |
| 4,359,476 | 11/1982 | Kaplan | 424/274 |
| 4,438,130 | 3/1984 | Kaplan . | |
| 4,460,600 | 7/1984 | Kaplan . | |
| 4,463,013 | 7/1984 | Collins . | |
| 4,598,087 | 7/1986 | Horwell . | |
| 4,656,182 | 4/1987 | Horwell . | |
| 4,663,343 | 5/1987 | Horwell . | |
| 4,677,122 | 6/1987 | Horwell . | |
| 4,737,493 | 4/1988 | Horwell . | |
| 4,906,655 | 3/1990 | Horwell et al. | 514/422 |

OTHER PUBLICATIONS

J. Pharmacol. Exp. Ther., 197:517-532 (1976).
J. Pharmacol. Exp. Ther., 224:7-12 (1983).

Primary Examiner—Robert A. Wax
Assistant Examiner—F. Tsung
Attorney, Agent, or Firm—Elizabeth M. Anderson

[57] ABSTRACT

The invention concerns a series of novel 2-amino-monomethoxycyclohexyl amides having analgesic and neuroprotective activity. The compounds bind selectivity to the kappa opioid receptor. Pharmaceutical compositions containing the compounds, methods of using them, and processes for preparing them are also disclosed.

6 Claims, No Drawings

2-AMINO-4 OR 5-METHOXYCYCLOHEXYL AMIDES USEFUL AS ANALGESICS

This application is a continuation of prior U.S. application No. 07/280,759 filed Dec. 6, 1988, now abandoned.

BACKGROUND OF THE INVENTION

The search for strong analgesics which also possess minimal potential for dependency has been among the highest priority efforts in pharmaceutical research. These research efforts have, to a great extent, involved chemical modification of the opiate structure and the discovery of novel compounds which possess morphine-like activity.

The concept of multiple opioid receptors has been supported by studies with nalorphine and a series of benzomorphans which display unusual pharmacological properties dissimilar from morphine, yet blocked by the opioid antagonists. [See, for example, W. R. Martin, et al., *J. Pharmacol. Exp. Ther.*, 197: 517–532 (1976).]

The existence of multiple types of opioid receptors is of importance because it suggests the possibility of separating the desirable analgesic and psychotherapeutic effects of a drug compound from the undesirable abuse potential or habituating effects.

U.S. Pat. No. 4,098,904 discloses certain cis- and trans-N-(2-aminocycloaliphatic) benzamide compounds having analgesic activity.

U.S. Pat. No. 4,145,435 describes certain 2-aminocycloaliphatic amide compounds as analgesics. In particular, trans-3,4-dichloro-N-methyl-N-[2-(1-pyrrolidinyl)cyclohexyl]benzeneacetamide is reported to possess selective kappa agonist activity, and therefore, to possess analgesic activity without attendant dependence liability. [See P. V. Vonvoigtlander, et al., *J. Pharmacol Exp. Ther.*, 224: 7–12 (1983).]

U.S. Pat. No. 4,212,878 discloses certain N-[(4-mono- or di-oxygen-group-substituted-1-aminocyclohex-1-yl)methyl]benzeneacetamides, particularly 2-(3,4-dichlorophenyl)-N-[[8-(1-pyrrolidinyl)-1,4-dioxaspiro[4.5]dec-8-yl]methyl]acetamide having analgesic properties.

U.S. Pat. No. 4,359,476 and its continuation-in-part 4,460,600 disclose certain N-[2-amino(oxy or thio group) substituted cycloaliphatic]benzeneacetamide and -benzamide compounds having the oxy- or thio group substituents on a cycloaliphatic ring carbon adjacent to either of the nitrogen-bearing carbon atoms of the cycloaliphatic ring. These compounds, having analgesic activity are typified by 4-bromo-N-[3-methoxy-2-(1-pyrrolidinyl)cyclohexyl]-N-methylbenzamide.

U.S. Pat. No. 4,598,087 and its divisional, U.S. Pat. No. 4,677,122, disclose certain oxy- or thioacetamides of trans-1,2-diaminocyclohexane having analgesic activity. These compounds are typified by trans-2-(2,3-dichlorophenoxy -N-methyl-N-[2-(1-pyrrolidinyl)cyclohexyl]acetamide.

U.S. Pat. No. 4,656,182 discloses certain trans-N-methyl-N-[2-(1-pyrrolidinyl)cyclohexyl]benzo[b]thiophene acetamides having analgesic activity.

U.S. Pat. No. 4,663,343 discloses certain trans-N-methyl-N-[2-(1-pyrrolidinyl)cyclohexyl]naphthalenyloxy- and naphthalenylthioacetamides having analgesic activity.

U.S. Pat. No. 4,737,493 discloses certain substituted phenoxy-, 1-, and 2-naphthalenyloxy, indenyl-, indolyl-, benzofuranyl-, and benzo[b]thiophenylcarboxamides of 7,8-(substituted-diamino)-1-oxaspiro[4.5]decanes useful as analgesic agents.

U.S. Pat. No. 4,463,013 discloses certain oxygen substituted amino-cyclohexyl-benzeneacetamides as diuretics.

U.S. Pat. No. 4,438,130 discloses certain mono-oxa-, thiaspiro-cyclic-benzeneacetamide and benzamide compounds useful as analgesics.

SUMMARY OF THE INVENTION

The invention relates to a novel series of 2-amino-4 or -5-monomethoxycyclohexyl amides which possess selective kappa receptor analgesic activity. The compounds show a surprising increase in activity in the nociceptive assay of the rat paw pressure test of M. B. Tyers, *Brit. J. Pharmacol.*, 69: 503–512 (1980) when compared with compounds known in the art.

The invention covers novel amides of formula

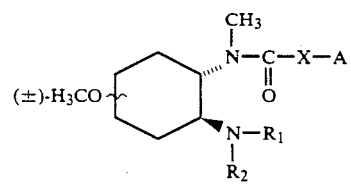

and the pharmaceutically acceptable acid addition salts thereof wherein X, $R_1$, $R_2$, and A are as defined herein below.

The invention also includes pharmaceutical compositions comprising an analgesically effective amount of the above compound in admixture with a pharmaceutically acceptable carrier or excipient and a method of treating pain in a patient suffering therefrom comprising administering to said patient the pharmaceutical composition in unit dosage form.

The invention further includes pharmaceutical compositions comprised of a neuroprotective amount of the above compound in admixture with a pharmaceutically acceptable carrier or excipient as well as a method of treating stroke and/or cerebral ischemia in a patient suffering therefrom.

The invention further includes methods for preparing compounds of formula I above.

DETAILED DESCRIPTION

The compounds of the present invention are represented by formula

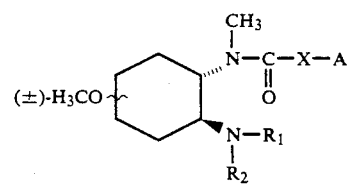

wherein the two nitrogen atoms attached to the cyclohexane moiety are trans to one another;

X is $CH_2$ or direct bond, $R_1$ is methyl, $R_2$ is selected from the group consisting of:

hydrogen, alkyl of from one to six carbon atoms,

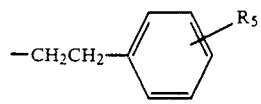

—CH₂H=CR₃R₄,
—CH₂C≡R₃,
-2- or 3-thienyl, or

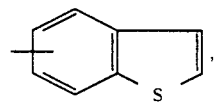

wherein R₃ and R₄ are each independently hydrogen or methyl,

R₅ is selected from the group consisting of:
hydrogen,
fluorine,
chlorine,
bromine,
lower alkyl, and
lower alkoxy; or R₁ and R₂ may be taken together with the nitrogen atom to which they are attached to form a ring

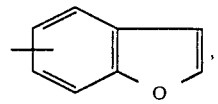

wherein n is an integer of from 3 to 8;
A is selected from the group consisting of:

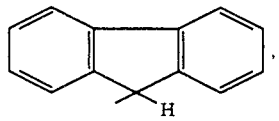

phenyl,
phenyl substituted with from one to four halogen atoms,
phenyl substituted with one or two alkyl groups of from one to four carbon atoms,
phenyl substituted with one or two alkoxy groups of from one to four carbon atoms, or
phenyl substituted with one or two alkyl groups of from one to four carbon atoms and one or two halogen atoms; or
a pharmaceutically acceptable acid addition salt thereof.

Preferred compounds of the present invention as those of formula I wherein X is CH₂ and A is

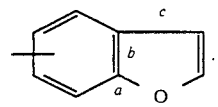

Other preferred compounds of the present invention are those of formula I wherein X is a direct bond and A is

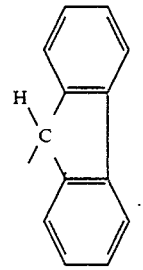

Particularly preferred compounds of the present invention are those of formula I wherein
X is CH₂, A is

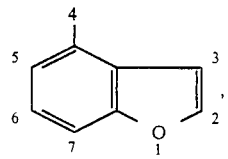

and
R₁ and R₂ may be taken together with the nitrogen to which they are attached to form a ring

—N   (CH₂)ₙ wherein n is an integer of from 3 to 8.

The most preferred compounds of the present invention are selected from the list consisting of:
(±)-(1α,2β,4β)-N-methyl-N-[4-methoxy-2-(1-pyrrolidinyl) cyclohexyl]-4-benzofuranacetamide,
(±)-(1α,2β,4α)-N-methyl-N-[4-methoxy-2-(1-pyrrolidinyl) cyclohexyl]-4-benzofuranacetamide,
(±)-(1α,2β,5β)-N-methyl-N-[5-methoxy-2-(1-pyrrolidinyl) cyclohexyl]-4-benzofuranacetamide,
(±)-(1α,2β,5α)-N-methyl-N-[5-methoxy-2-(1-pyrrolidinyl) cyclohexyl]-4-benzofuranacetamide,
(±)-(1α,2β,4α)-N-methyl-N-[4-methoxy-2-(1-pyrrolidinyl) cyclohexyl]-9H-fluorene-9-carboxamide, and
(±)-(1α,2β,5β)-N-methyl-N-[5-methoxy-2-(1-pyrrolidinyl) cyclohexyl]-9H-fluorene-9-carboxamide.

A method for preparing compounds of formula I wherein A is

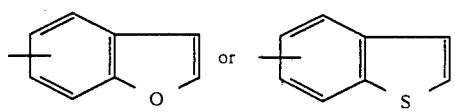

which comprises reacting an amine compound of formula

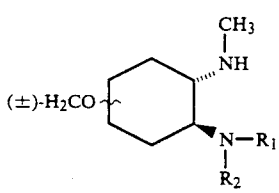

wherein $R_1$ and $R_2$ are as defined above with A-X-CH$_2$COB wherein B is —Cl, —OH, —OC$_6$F$_5$ or

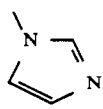

and, if desired, converting the product to a pharmaceutically acceptable acid addition salt thereof.

A method for preparing compounds of formula I wherein A is

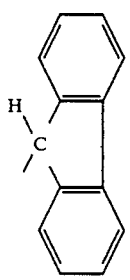

which comprises reacting an amine compound of formula

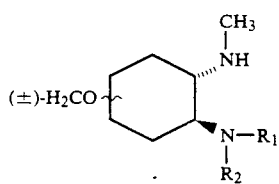

wherein $R_1$ and $R_2$ are as defined above with

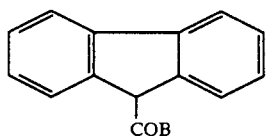

wherein B is —OH, —Cl or

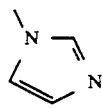

or OC$_6$F$_5$ and, if desired, converting the product to a pharmaceutically acceptable salt thereof.

The compounds of the present invention include solvates, hydrates, and pharmaceutically acceptable acid addition salts of the basic compounds of formula I above.

By virtue of the basic nitrogen on the cyclohexane moiety, pharmaceutically acceptable salts of compounds of the present invention may be prepared by reaction with appropriate acids. Suitable acids for the formation of pharmaceutically acceptable salts of the compounds of this invention form a class well known to practitioners of the pharmaceutical formulation arts (cf. S. M. Berge, et al., "Pharmaceutical Salts" in *J. Pharm. Sci.*, 66: 1–19 (1977)), and include such acids as hydrochloric, hydrobromic, hydriodic, sulfuric, nitric, phosphoric, acetic, benzoic, citric, maleic, tartaric, succinic, gluconic, ascorbic, sulphamic, oxalic, pamoic, methanesulfonic, benzenesulfonic, ethanesulfonic, hydroxyethanesulfonic, and related acids and mixtures thereof.

The salts are generally prepared by reacting the free base with one equivalent of the desired acid in an appropriate unreactive solvent, followed by collection of the salt by filtration or recovery upon removal of the solvent. The free base may be regenerated, if desired, by reaction of the salt with one equivalent of a base such as sodium hydroxide, sodium bicarbonate, sodium carbonate, and the like. The salts may differ from the free base form of compounds of this invention in properties such as melting point and solubility in polar solvents, but are otherwise considered equivalent for the purposes of this invention.

The compounds of the present invention contain three or more asymmetric carbon atoms. The compounds exist in various stereo- and regio-isomeric forms and mixtures thereof. The present invention contemplates all stereo- and regio-isomeric forms of the compounds of formula I above. Both the (+) and (−) and the (±) are contemplated by the invention.

The individual stereo compounds or enantiomers are obtained, if desired, from a mixture of different forms by known methods of resolution such as the formation of diastereomers followed by recrystallization.

The compounds of the present invention possess significant analgesic activity with the potential for minimum dependence liability due to their selective kappa opioid receptor properties. In addition to producing analgesia, compounds which are selective kappa agonists, such as the compounds of this invention, also cause opioid receptor-mediated sedation, diuresis, and corticosteroid elevation. Accordingly, the compounds of this invention may also be useful as diuretics and psychotherapeutic agents as well as analgesics.

The compounds of the present invention also have application in congestive heart failure, advanced hepatic cirrhosis, nephrotic syndrome, chronic renal failure, trauma associated with surgery, emotional and physical stress, endocrine disorders, syndrome of inappropriate antidiuretic hormone secretion and therapy with certain pharmacologic drug agents such as certain sulphonyl ureas, certain biguanides such as phenformin and metformin, clofibrate, certain tricycles such as carbamazepine, amitriptyline, thiothixene, fluphenazine and thioridazine, certain antineoplastic agents, certain analgesics and certain natriuretic diuretics.

The compounds of the present invention also have neuroprotective indications. As such they are useful in the treatment of stroke and the treatment of cerebral ischemia (P. F. Von Voightlander in *Brain Research* 435: 174–180 (1987)) and A. H. Tang, et al. in *Brain Research* 403: 52–57 (1987)).

Representative compounds of the present invention demonstrate positive activity in standard laboratory analgesic tests in animals such as mice. The doses for several representative compounds of this invention in the standard rat paw pressure analgesia test M. B. Tyers, *Brit. J. Pharmacol.*, (1980), 69: 503-512 are presented in Table I below, the last column.

TABLE I

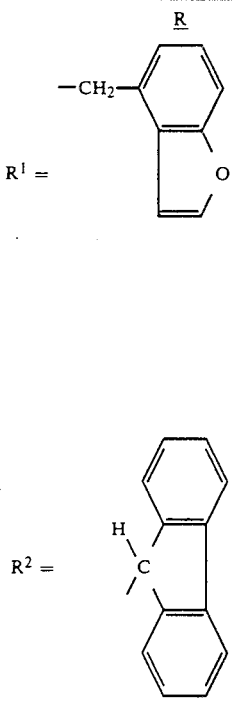

| Compound Number | Structure (Position of OMe) | R | Opioid Binding ($K_i$ nM) | | | Rat Paw Pressure MPE$_{50}$ (mg/kg) I.V. |
|---|---|---|---|---|---|---|
| | | | kappa | mu | mu/k | |
| 10 | 4-β | R$^1$ | 7.1 ± 4 | 3300 ± 1900 | 465 | 0.07 |
| 5 | 4-α | R$_1$ | 22 ± 6 | 2200 ± 200 | 100 | 0.07 |
| 6 | 5-β | R$^1$ | 135 ± 30 | 11000 ± 4800 | 81 | 5.6 |
| 7 | 5-α | R$^1$ | 24 ± 4 | 4300 ± 400 | 179 | 1.5 |
| 8 | 4-α | R$^2$ | 0.84 ± 0.9 | 28 ± 1.3 | 33 | — |
| 9 | 5-β | R$^2$ | 6.7 ± 1.3 | 2130 ± 176 | 318 | >1 |

$K_i$ values represent the mean ± (standard error of the mean) from concentration-response curves performed in triplicate from each of at least two separate experiments.

MPE$_{50}$ values represent the dose required to produce 50% of the maximum possible analgesic effect. They are derived from a single experiment with six animals per dose level.

Representative compounds of the present invention were also tested in vitro to determine the extent of opioid receptor binding, and were found to bind selectively to the kappa opioid receptor site with evidence of little or no binding to the mu or delta opioid receptors.

Measurement of the kappa opioid receptor binding activity of compounds of the present invention was made by the following method. Guinea pig brain homogenates were prepared fresh daily utilizing the method of Gillan et al. *Br. J. Pharmacol.* (1980) 70: 481-490.

The binding of tritiated etorphine to brain homogenates was measured in the presence unlabeled competitor compounds of the present invention with 200 nanomolar D-alanine-D-leucine-enkephalin (acronym DADLE) and 200 nanomolar D-ala-MePheGly-ol-enkephalin (acronym DAGO) added to saturate the delta and mu opioid receptors, respectively. The reaction was terminated by rapid filtration and the radioactivity bound to the filters counted by liquid scintillation spectrophotometry.

Measurement of the mu and delta opioid receptor binding activity of the compounds of this invention was made by the following method. Guinea pig brain homogenates were freshly prepared daily by the method of Gillan, et al., cited above.

Homogenates were incubated for 150 minutes at 0° C. with either tritiated DAGO to measure mu receptor binding activity, or with tritiated DADLE in the presence of a ten-fold excess of unlabeled DAGO to measure delta opioid receptor binding. Nonspecific binding was determined in the presence of 10$^{-6}$ molar DAGO and 10$^{-6}$ molar DADLE.

Reactions were terminated by rapid filtration and the radioactivity bound to the filters counted by liquid scintillation spectrophotometry.

The data were analyzed by the methods of Scatchard, *Ann. N.Y. Acad. Sci.*, 51: 660-672 (1949) and Hill, *J. Physiol.*, 40: IV-VIII (1910). The inhibition of the binding of tritiated etorphine, DAGO and DADLE by cold ligands was determined from the regression of log percentage inhibition of specific binding or log concentration of cold ligand. The inhibition constant, Ki, was calculated from the equation:

$$K_i = \frac{IC_{50}}{1 + [L]/K_D}$$

where [L] is the concentration of the labeled ligand and $K_D$ is the equilibrium dissociation constant.

Scheme I below illustrates chemical synthesis of the compounds of the present invention. All compounds are racemic mixtures. They are prepared by epoxidizing 4-methoxycyclohexene [Gogek, Moir and Purves, *Can. J. Chem.*, 29: 946 (1951)] by the action of m-chloroperbenzoic acid in dichloromethane to yield the 4-methoxycyclohexene epoxides (1). Reaction of (1) with N-benzylmethylamine in alcohol yields a mixture of three isomeric amino alcohols (2). This mixture of amino alcohols, (2), is treated with methanesulphonyl chloride and subsequently with pyrrolidine to yield a mixture of N-benzyldiamines, (3). This mixture of N-benzyldiamines, (3), is dissolved in alcohol and then catalytically hydrogenated to form a mixture of diamines (4). This mixture of diamines, (4), may then be reacted with an ester of 9-fluorenylcarboxylic acid to form the desired product which may then be separated by known means.

Alternatively, the mixture of diamines (4), may be reacted with 4-benzofuranacetyl chloride to yield a mixture of isomers of the desired product which may be separated by known means.

(10) was prepared from the epoxides (1) by an analogous procedure to that described above for (5), (6), and (7) except that pyrrolidine was used instead of N-benzylmethylamine and vice versa.

SCHEME I
(all compounds are racemic)
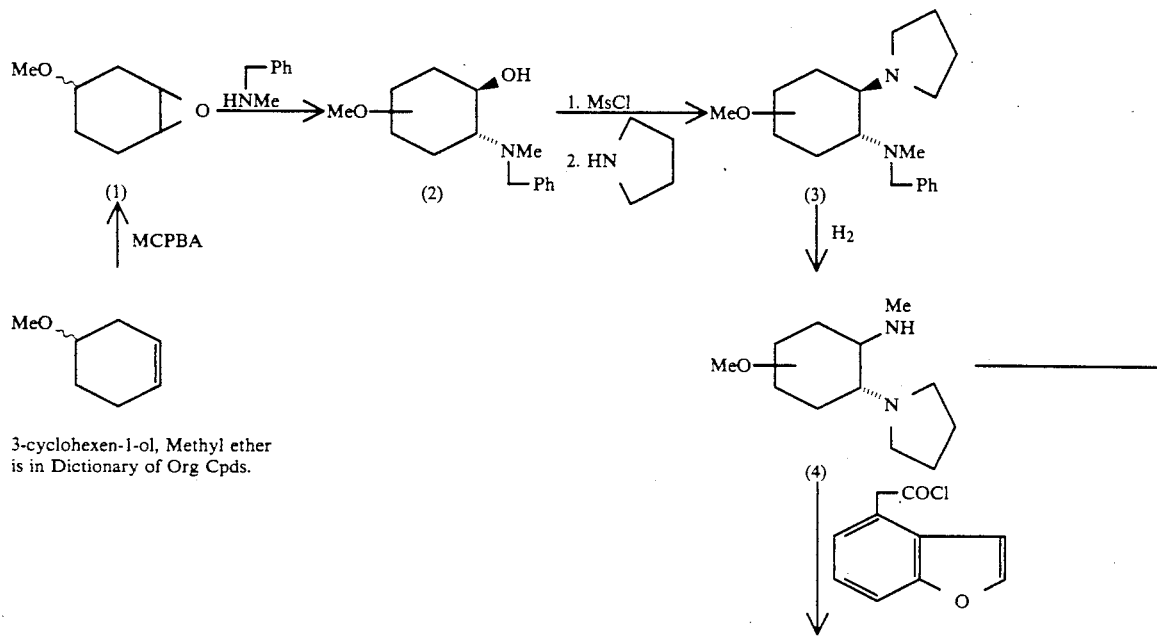
3-cyclohexen-1-ol, Methyl ether is in Dictionary of Org Cpds.
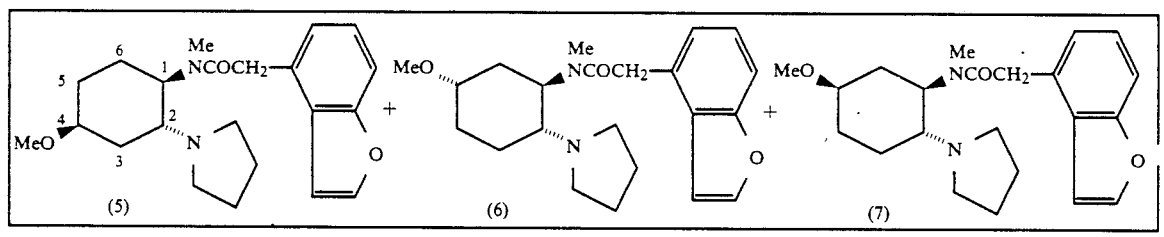
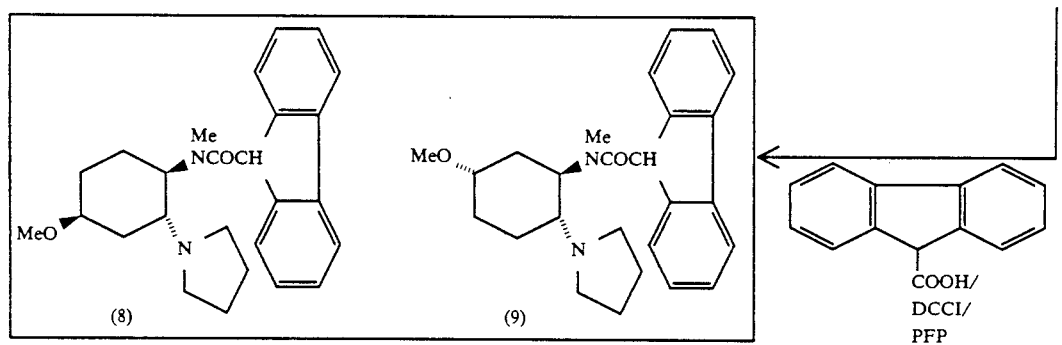
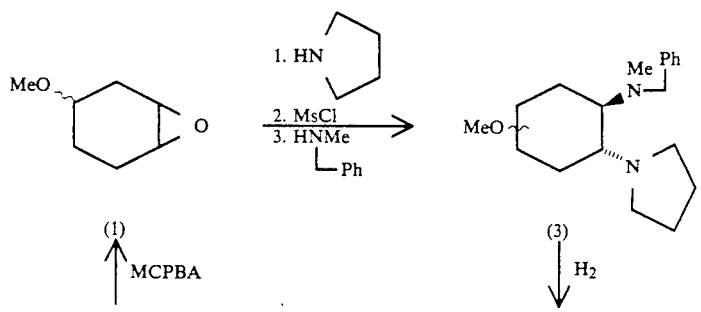

-continued
SCHEME I
(all compounds are racemic)

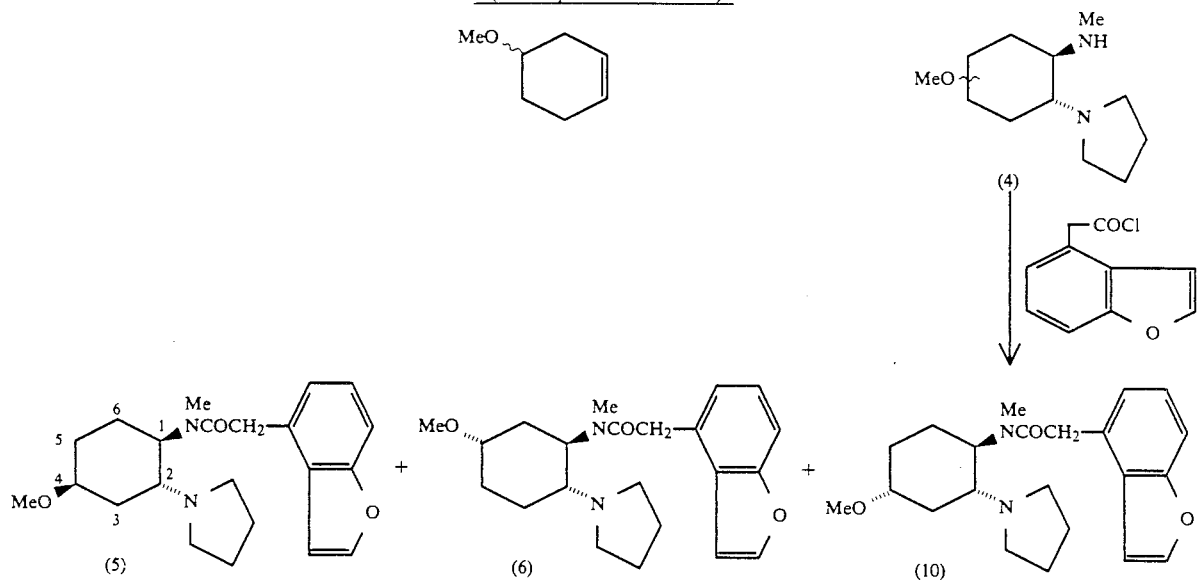

Compounds of the present invention and/or their nontoxic, pharmaceutically acceptable salts may be administered to mammals orally in combination with conventional compatible carriers in solid or in liquid form. These oral pharmaceutical compositions may contain conventional ingredients such as binding agents selected from syrups, acacia, gelatin, sorbitol, tragacanth, polyvinylpyrrolidone, and mixtures thereof. The compositions may further include fillers such as lactose, mannitols, starch, calcium phosphate, sorbitol, methylcellulose, and mixtures thereof.

These oral compositions may also contain lubricants such as magnesium stearate, high molecular weight polymers such as polyethylene glycol, high molecular weight fatty acids such as stearic acid, silica, or agents to facilitate disintegration of the solid formulation such as starch, and wetting agents such as sodium lauryl sulfate.

The solid oral compositions may take any convenient form such as tablets, lozenges, capsules, or dry powders which may be reconstituted with water or other suitable liquid prior to administration.

Liquid form pharmaceutical compositions may take the form of solutions, suspensions, or emulsions. The liquid forms may contain flavorants, sweeteners, and/or preservatives such as alkyl p-hydroxybenzoates. They may further contain suspending agents such as sorbitol, glucose, or other sugar syrups, methyl-, hydroxymethyl- or carboxymethylcellulose, and gelatin, emulsifying agents such as lecithin or sorbitol monooleate, and conventional thickening agents.

Liquid compositions may optionally be encapsulated in, for example, gelatin capsules in an effective amount.

The compounds of the invention may also be administered to mammals rectally in the form of suppositories. For preparing suppositories, a low-melting wax such as a mixture of fatty acid glycerides or cocoa butter is first melted, and the active ingredient is dispersed homogeneously in the melt. The mixture is then poured into convenient sized molds and allowed to cool and solidify.

Preferably, the pharmaceutical compositions of this invention are in unit dosage form. In such form, the preparation is subdivided into unit doses containing appropriate amounts of the active component. The unit doses can be a packaged preparation with the package containing discrete quantities of the preparation. For example, the package may take the form of packaged tablets, capsules, and powders in envelopes, vials, or ampoules. The unit dosage form can also be a capsule, cachet, or tablet itself or can be the appropriate number of any of these in package form.

The quantity of active compound in a unit dose of preparation may be varied or adjusted from about 0.01 mg to about 350 mg according to the particular application and the potency of the active ingredient.

When employed systematically in therapeutic use as analgesic agents in the pharmaceutical method of this invention, the compounds are administered at doses of from about 0.0001 mg to about 2.0 mg of active compound per kilogram of the recipient.

The following examples are provided to enable one skilled in the art to practice the present invention. These examples are not intended in any way to limit the scope of the invention but are intended as illustrative thereof.

EXAMPLE 1

4-Methoxycyclohexane epoxide (1)

m-Chloroperoxybenzoic acid (3.5 g, 20 mmol) in 1:1 dichloromethane-carbon tetrachloride (70 ml) was added over 25 minutes to a stirred solution of 4-methoxycyclohexene (2.0 g, 18 mmol) in carbon tetrachloride (10 ml) at $-5°$ C. After five hours the mixture was allowed to warm to room temperature and after two hours the slurry was filtered. The filtrate was washed with 5% aqueous sodium bisulphite (40 ml) then saturated aqueous sodium carbonate (2×40 ml).

The resulting solution was dried ($K_2CO_3$) and distilled using a vigreaux column at atmospheric pressure to give the epoxides (1) as a mixture of two diastereoisomers (1.0 g, 7.8 mmol), 43%), bp 175°–176° C. (760 mm Hg); i.r. (neat) 2938, 1104 $cm^{-1}$; δ ($CDCl_3$, 300 $MH_z$) 3.22 (1H,m); 3.24 (s) and 3.22 (s) together (3H); 3.05

(2H,m), 2.3-1.2 (6H,m); m/e (EI+) 129 (11%), 111 (35%), 97 (65%), 58 (100%);

Anal. $C_7H_{12}O_2$ requires C, 65.60; H, 9.44.
Found C, 65.57; H, 9.60%.

EXAMPLE 2

Amino alcohols (2)

The epoxides (1) (2.0 g, 15.6 mmol) and N-benzylmethylamine (3.0 g, 25 mmol) were dissolved in propan-2-ol (10 ml) and heated under reflux for 20 hours. The resulting solution was distilled to give the amino alcohols (2) as a mixture of three isomers (3.2 g, 13 mmol, 83%), bp 133°–134° C./ 0.05 mbar; i.r. (neat) 3460, 2939, 2866 cm$^{-1}$; δ (CDCl$_3$, D$_2$O) 7.3 (5H,m); 4.0-2.7 (7H,m, strong s at 3.36, 3.30, 3.29); 2.4-1.2 (10H,m, strong s at 2.19, 2.18, 2.15); m/e (EI+) 249 (10%), 218 (8%), 190 (100%);

Anal. $C_{15}H_{23}NO_2$ requires C, 72.25; H, 9.30; N, 5.62.
Found C, 72.13; H, 9.22; N, 5.56%. $^1$H nmr spectra of the individual isomers were obtained after separation by silica gel chromatography using 20:1 dichloromethane-methanol. δ (CDCl$_3$, D$_2$O) Isomer A: 7.24 (5H,m), 3.61 (1H,d,J=14); 3.45 (1H,J=14); 3.43 (1H,m); 3.36 (3H,s); 3.18 (1H,m); 2.36 (1H,m); 2.19 (3H,s); 2.27-1.99 (3H,m); 1.22 (3H,m). Isomer B: 7.28 (5H,m); 3.70 (1H,d,J=15 Hz); 3.65 (1H,m); 3.45 (1H,m); 3.44 (1H,d,J=15 Hz); 3.30 (3H,s); 2.83 (1H,m); 2.15 (3H,s); 2.20-1.85 (3H,m); 1.60 (1H,m); 1.30 (2H,m). Isomer C: 7.28 (5H,m); 3.79 (1H,m); 3.74 (1H,d,J=15 Hz); 3.55 (1H,m); 3.45 (1H,d,J=15 Hz); 3.29 (3H,s); 2.42 (2H,m); 2.18(3H,s); 2.05 (1H,m); 1.55 (2H,m); 1.30 (2H,m).

EXAMPLE 3

N-Benzyl diamines (3)

The diastereoisomeric mixture of amino alcohols (2) (8.0 g, 32 mmol) was dissolved in dichloromethane (105 ml) and triethylamine (7.1 ml), cooled to −10° C., and treated with methanesulphonyl chloride (2.7 ml, 35 mmol) dropwise such that the temperature remained below −5° C. After 1.5 hours the mixture was concentrated in vacuo to a volume of 20 ml and treated with pyrrolidine (22 ml, 260 mmol) under reflux for 1.5 hours. The resulting mixture was poured into aqueous sodium carbonate (700 ml) and extracted with dichloromethane (3×100 ml) to give, after concentration, an orange oil (15 g) which was distilled to give the N-benzyl diamines (3) as a mixture of three (racemic) isomers (9.3 g, 31 mmol, 97%); bp 122°–155° C./0.2 mbar; i r. (neat) 2936, 2791 cm$^{-1}$; m/e (EI+) 303 (5%). 287 (10%), 270 (10%), 84 (100%); δ (CDCl$_3$, D$_2$O, 300 MHz); 7.30 (5H,m); 3.65 (2H,s); 3.75-3.50 (1H,m); 3.36 (s) and 3.32 (s) and 3.29 (s) together are (3H); 2.19 (s) and 2.17 (s) and 2.15 (s) together are (3H); 3.10-1.00 (16H,m).

Anal. $C_{19}H_{30}N_2O.0.33H_2O$ requires C, 74.00; H, 10.02;
N, 9.08.
Found C, 73.97; H, 9.78; N, 8.82%.

EXAMPLE 4

Diamines (4)

The N-benzyl diamines (3) (3.5 g, 12 mmol) were dissolved in ethanol (50 ml) and treated with 20% palladium hydroxide on carbon (0.94 g) and hydrogen at 50 psi at 60° C. for two hours. The mixture was filtered through kieselguhr and distilled to give the diamines (4) as a mixture of three (racemic) isomers (1.4 g, 6.6 mmol, 55%); bp 84°–85° C./0.3 mbar; i.r. (neat) 3402, 2942 cm$^{-1}$; m/e (EI+) 197 (5%), 180 (10%), 84 (100%); δ (CDCl$_3$, D$_2$O, 300 MHz), 3.36 (s) and 3.31 (s) and 3.28 (s) together are (3H); 2.38 (s) and 2.37 (s) together are (3H); 3.7 (1H,m); 2.8-0.9 (17H,m). An analytically pure sample was obtained by treating (4) (212 mg, 1.0 mmol) with p-toluene sulphonic acid (190 mg, 1.0 mmol) in propan-2-ol (1 ml) to give a white solid which was recrystallized from propan-2-ol/ diethyl ether to give the mono-p-toluenesulphonate salt (200 mg, 0.50 mmol, 50%), mp 120°–136° C.

Anal. $C_{12}H_{24}N_2O.C_7H_8SO_3$ requires C, 59.35; H, 8.39; N, 7.29;
S, 8.34.
Found C, 58.95; H, 8.24; N, 6.99; S, 8.42%.

EXAMPLE 5

(±)-(1α,2β,4α)-N-[4-methoxy-2-(1-pyrrolidinyl) cyclohexyl]-N-methyl-4-benzofuranacetamide (5);

(±)-(1α,2β,5β)-N-[5-methoxy-2-(1-pyrrolidinyl) cyclohexyl]-N-methyl-4-benzofuranacetamide (6);

(±)-(1α,2β,5α)-N-[5-methoxy-2-(1-pyrrolidinyl) cyclohexyl]-N-methyl-4-benzofuranacetamide (7).

4-Benzofuranacetic acid (0.757 g, 4.3 mmol) was dissolved in thionyl chloride (3 ml) and heated under reflux for 70 minutes. The resulting solution was concentrated in vacuo to furnish an oil which was dissolved in dichloromethane (10 ml), cooled to 0° C., and treated with a solution of the diamines (4) (0.80 g, 3.8 mmol) in dichloromethane (5 ml). The mixture was stirred at room temperature for 10 minutes and chromatographed on silica gel using 10:1 dichloromethane/methanol to give (±)-(1α,2β,5β)-N-[5-methoxy-2-(1-pyrrolidinyl)-cyclohexyl-N-methyl-4-benzofuranacetamide (6) (150 mg, 0.41 mmol, 11%); i.r. (neat) 1642 cm$^{-1}$; m/e (CI+) 371 (3%); 275 (100%); δ (CDCl$_3$, 300 MHz) 7.6-6.9 (5H,m); 4.78 (1H,m,C$_1$-H); 3.95 (2H,m,CH$_2$), 3.56 (m) and 3.46 (m) together are 1H, C$_5$-H); 3.33 (s) and 3.13 (s) together are (3H); 2.83 (s) and 2.82 (s) together are (3H), 2.80-1.20 (15H,m). (±)-(1α-2β,4α) -N-[4-methoxy-2-(1-pyrrolidinyl)cyclohexyl]-N-methyl-4-benzofuranacetamide (5) (100 mg, 0.27 mmol, 7%); i.r. (neat) 1635 cm$^{-1}$; m/e (CI+) 371 (100%); δ (CDCl$_3$, 300 MHz) 7.55-6.90 (5H,m); 4.60 (1H,dt,J=12,5 Hz,C$_1$-H); 3.95 (2H,m,CH$_2$); 3.7-3.4 (1H,m,C$_4$-H); 3.29 (s) and 3.24 (s) together are (3H); 3.09 (1H,dt,J=12,5Hz,C$_2$-H); 2.83 (s) and 2.82 (s) together are (3H); 2.65-1.25 (14H,m). (±)-(1α,2β,5α)-N-[5-methoxy-2-(1-pyrrolidinyl)cyclohexyl]-N-methyl-4-benzofuranacetamide (7) (92 mg, 0.25 mmol, 7%); i.r. (neat) 1640 cm$^{-1}$; m/e (CI+) 371 (100%), 339 (38%); δ (CDCl$_3$, 300 MHz) 7.65-6.85 (5H,m); 4.65 (1H,m,C$_1$-H); 3.95 (2H,m,CH$_2$); 3.33 (3H,s); 3.70-3.20 (2H,m,C$_5$-H and C$_2$-H); 2.83 (s) and 2.80 (s) together are (3H); 2.80-0.80 (14H,m).

An analytically pure sample was obtained by treating (6) (100 mg) in diethyl ether (10 ml) with hydrogen chloride. The resulting solution was filtered to give the monohydrochloride salt (100 mg); mp 102°–106° C.
Anal. $C_{22}H_{30}N_2O_3.HCl.0.77 H_2O$ requires C, 62.79; H, 7.79;
N, 6.66; Cl, 8.42.
Found C, 62.79; H, 7.69; N, 6.64; Cl, 8.20%.

EXAMPLE 6

(±)-(1α,2β,4α)-N-[4-methoxy-2-(1-pyrrolidinyl)cyclohexyl]-N-methyl-9H-fluorene-9-carboxamide (8) and (±)-(1α,2β,5β)-N-[5-methoxy-2-(1-pyrrolidinyl)cyclohexyl]-N-methyl-9H-fluorene-9-carboxamide (9).

9-Fluorenyl carboxylic acid (210 mg, 1.0 mmol) and pentafluorophenol (184 mg, 1.0 mmol) were dissolved in ethyl acetate (5 ml) and stirred at 0° C. After five minutes dicyclohexylcarbodiimide (Aldrich Chemical Company) (168 mg, 1.0 mmol) was added and after a further one hour the mixture was treated with the diamines (4) (182 mg, 0.87 mmol) (described above) and allowed to warm to room temperature for one hour. The mixture was filtered and chromatographed on silica gel using 20:1 dichloromethane-methanol to give (8) (33.4 mg, 0.083 mmol, 10%); i.r. (neat) 1632 cm$^{-1}$; δ (CDCl$_3$, NaOD) 7.80-7.20 (8H,m); 4.57 (1H,dt,J=13,5 Hz,C$_1$-H); 3.25 (3H,s); 3.60-1.20 (19H,m); m/e (EI$^+$) 404 (0.5%), 389 (2%), 373 (3%), 110 (100%). (9) (34 mg, 0.084 mmol, 10%); i.r. (neat) 1633 cm$^{-1}$; δ (CDCl$_3$, NaOD) 7.80-7.20 (8H,m); 4.75 (1H,m,C$_1$-H); 3.32 (3H,s); 3.60-1.20 (19H,m).

EXAMPLE 7

(±)-(1α,2β,4β)-N-[4-methoxy-2-(1-pyrrolidinyl)cyclohexyl]-N-methyl-4-benzofuranacetamide (10)

(10) was prepared from the epoxides (1) by an analogous procedure to that described above for (5), (6), and (7) except that pyrrolidine was used instead of N-benzylmethylamine and vice versa. The epoxides (1) (2.0 g, 16 mmol) and pyrrolidine (2.0 g, 28 mmol) were heated to 65° C. for 19 hours then concentrated in vacuo to give an oil (3.0 g) which was dissolved in dichloromethane (30 ml) and treated with triethylamine (2.5 ml, 18 mmol) and methanesulphonyl chloride (1.28 ml, 16.5 mmol) at 0° C. for 1.5 hours. The mixture was added to dichloromethane (70 ml) and washed with water (3×70 ml), dried (MgSO$_4$), and evaporated in vacuo to give an oil (3.2 g). This oil was dissolved in N-benzylmethylamine (7 ml), heated to 85°-90° C. for 1.5 hours, poured into aqueous potassium carbonate, and extracted with dichloromethane (50 ml). Bulb to bulb distillation (oven temperature) 170°-225° C./0.05 mbar, gave a mixture of the diamines (3) (1.1 g, 3.6 mmol, 22%).

This mixture of diamines (3) (1.1 g, 3.6 mmol) was dissolved in ethanol (30 ml) and treated with 20% palladium hydroxide on carbon (0.21 g) and hydrogen at 53 psi and 40° C. for five hours to give, as described above, a mixture of the diamines (4) (0.60 g, 2.8 mmol, 78%). This mixture of diamines (0.60 g, 2.8 mmol) was treated with 4-benzofuranacetyl chloride [generated from 4-benzofuranacetic acid (0.6 g, 3.5 mmol) as described above] to give (6) (130 mg, 0.35 mmol, 10%); (5) (25 mg, 0.068 mmol, 2%); and (10) (25 mg, 0.068 mmol, 2%), i.r. (neat) 1635 cm$^{-1}$; m/e (CI$^+$) 371 (67%), 275 (65%), 159 (100%); δ (CDCl$_3$, NaOD) 7.65-6.85 (5H,m); 4.55 (1H,br,C$_1$-H); 3.95 (2H,m,CH$_2$); 3.34 (s) and 3.31 (s) together are (3H); 2.79 (s) and 2.77 (s) together are (3H); 3.60-0.80 (16H,m).

We claim:
1. A compound of formula

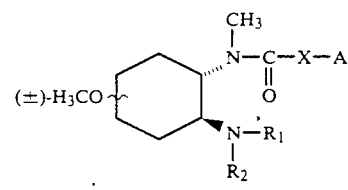

wherein (±)—H,CO— is attached at the 4- or 5-position and wherein the two nitrogen atoms attached to the cyclohexane moiety are trans to one another;
X is CH$_2$ or direct bond,
R$_1$ is methyl,
R$_2$ is selected from the group consisting of:
  hydrogen,
  alkyl of from one to six carbon atoms,

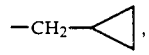

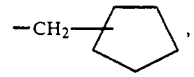

—CH$_2$CH=CH$_3$R$_4$,
—CH$_2$C≡R$_3$,
-2- or 3-thienyl, or

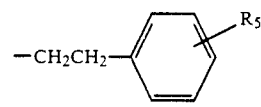

wherein R$_3$ and R$_4$ are each independently hydrogen or methyl,
R$_5$ is selected from the group consisting of:
  hydrogen,
  fluorine,
  chlorine,
  bromine,
  lower alkyl, and
  lower alkoxy;
or R$_1$ and R$_2$ may be taken together with the nitrogen atom to which they are attached to form a ring

wherein n is an integer of from 3 to 8;
A is selected from the group consisting of:

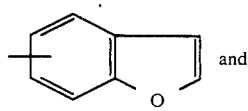

and

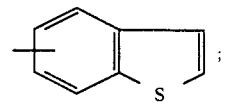

or a pharmaceutically acceptable acid addition salt thereof.

2. A compound according to claim 1 wherein X is CH₂ and A is

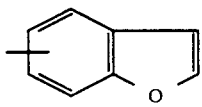

3. A compound according to claim 2 wherein A is

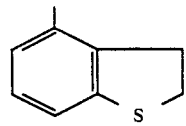

4. A compound selected from the group consisting of
(±)-(1α,2β,4β)-N-[4-methoxy-2-(1-pyrrolidinyl) cyclohexyl]-N-methyl-4-benzofuranacetamide,
(±)-(1α,2β,4α)-N-[4-methoxy-2-(1-pyrrolidinyl) cyclohexyl]-N-methyl-4-benzofuranacetamide,
(±)-(1α,2β,5β)-N-[5-methoxy-2-(1-pyrrolidinyl) cyclohexyl]-N-methyl-4-benzofuranacetamide, and
(±)-(1α,2β,5α)-N-[5-methoxy-2-(1-pyrrolidinyl) cyclohexyl]-N-methyl-4-benzofuranacetamide.

5. A pharmaceutical composition useful for treating pain in a mammal comprising an analgesically effective amount of a compound as claimed in claim 1 together with a pharmaceutically acceptable carrier.

6. A method of treating pain in a mammal which comprises administering to said mammal a pharmaceutical composition according to claim 5.

* * * * *

UNITED STATES PATENT AND TRADEMARK OFFICE
CERTIFICATE OF CORRECTION

PATENT NO. : 5,051,428
DATED : September 24, 1991
INVENTOR(S) : David C. Horwell et al It is certified that error appears in the above-identified patent and that said Letters Patent is hereby corrected as shown below:

Column 16, line 10, "H,CO-" should read "H$_3$CO-".

Column 16, line 52, structure should be as follows:

Signed and Sealed this

Fifth Day of January, 1993

Attest:

DOUGLAS B. COMER

Attesting Officer

Acting Commissioner of Patents and Trademarks